United States Patent
Middleton

(10) Patent No.: US 8,562,634 B2
(45) Date of Patent: Oct. 22, 2013

(54) INSTRUMENTS AND METHODS FOR REDUCING AND STABILIZING BONE FRACTURES

(75) Inventor: Lance M. Middleton, Soddy Daisy, TN (US)

(73) Assignee: Cavitech, LLC, Scottsdale, AZ (US)

( * ) Notice: Subject to any disclaimer, the term of this patent is extended or adjusted under 35 U.S.C. 154(b) by 0 days.

(21) Appl. No.: 13/405,061

(22) Filed: Feb. 24, 2012

(65) Prior Publication Data

US 2012/0158142 A1 Jun. 21, 2012

Related U.S. Application Data

(63) Continuation of application No. 11/140,413, filed on May 27, 2005, now Pat. No. 8,142,462.

(60) Provisional application No. 60/575,635, filed on May 28, 2004.

(51) Int. Cl.
*A61B 17/32* (2006.01)

(52) U.S. Cl.
USPC .............................. 606/170; 606/79; 606/178

(58) Field of Classification Search
USPC ........... 606/79, 80, 83–85, 92–94, 86 R, 170, 606/171, 178, 183; 623/17.11–17.12
See application file for complete search history.

(56) References Cited

U.S. PATENT DOCUMENTS

| | | | |
|---|---|---|---|
| 1,685,380 A | 9/1928 | Shultz | |
| 3,030,951 A | 4/1962 | Mandarino | |
| 3,112,743 A | 12/1963 | Cochran et al. | |
| 3,320,957 A | 5/1967 | Sokolik | |
| 4,065,817 A | 1/1978 | Branemark et al. | |
| 4,313,434 A | 2/1982 | Segal | |
| 4,369,772 A | 1/1983 | Miller | |
| 4,403,606 A | 9/1983 | Woo et al. | |
| 4,403,607 A | 9/1983 | Woo et al. | |
| 4,493,317 A | 1/1985 | Klaue et al. | |
| 4,494,535 A | 1/1985 | Haig | |

(Continued)

FOREIGN PATENT DOCUMENTS

| | | |
|---|---|---|
| DE | 3914164 C1 | 1/1991 |
| EP | 0442137 A1 | 8/1991 |

(Continued)

OTHER PUBLICATIONS

Communication pursuant to Article 94(3) EPC dated Jun. 1, 2010 for Application No. EP 08769546.6.

(Continued)

*Primary Examiner* — Mary C. Hoffman
*Assistant Examiner* — Tara Carter
(74) *Attorney, Agent, or Firm* — Gardere Wynne Sewell LLP

(57) ABSTRACT

Instruments and methods for reducing and stabilizing bone fractures are presented, which include providing a cavity in bone, such as a vertebra, wherein the cavity is proximate to an endplate of the bone, such as a vertebra endplate, and wherein the cavity extends radially from a passage into the cavity. The methods further include providing a device, such as an inflatable device, into the cavity and manipulating the device for expansion. The cavity may be expanded thereby reducing and/or stabilizing the fracture. The fracture may be further reduced and/or stabilized by adding a material into the cavity.

18 Claims, 7 Drawing Sheets

(56) References Cited

U.S. PATENT DOCUMENTS

| | | | |
|---|---|---|---|
| 4,503,848 A | 3/1985 | Caspar et al. |
| 4,513,744 A | 4/1985 | Klaue et al. |
| 4,653,489 A | 3/1987 | Tronzo |
| 4,743,260 A | 5/1988 | Burton |
| 4,751,922 A | 6/1988 | DiPietropolo |
| 4,773,406 A | 9/1988 | Spector et al. |
| 4,794,918 A | 1/1989 | Wolter et al. |
| 4,969,888 A | 11/1990 | Scholten et al. |
| 5,002,544 A | 3/1991 | Klaue et al. |
| 5,014,124 A | 5/1991 | Fujisawa |
| 5,019,078 A | 5/1991 | Perren et al. |
| 5,030,201 A | 7/1991 | Palestrant |
| 5,053,036 A | 10/1991 | Perren et al. |
| 5,062,845 A | 11/1991 | Kuslich et al. |
| 5,085,660 A | 2/1992 | Lin |
| 5,102,413 A | 4/1992 | Poddar |
| 5,108,404 A | 4/1992 | Scholten et al. |
| 5,116,336 A | 5/1992 | Frigg |
| 5,147,361 A | 9/1992 | Ojima et al. |
| 5,151,103 A | 9/1992 | Tepic et al. |
| 5,211,651 A | 5/1993 | Reger et al. |
| 5,275,601 A | 1/1994 | Gogolewski et al. |
| 5,303,718 A | 4/1994 | Krajicek |
| 5,344,421 A | 9/1994 | Crook |
| 5,360,432 A | 11/1994 | Shturman |
| 5,364,399 A | 11/1994 | Lowery et al. |
| 5,376,100 A | 12/1994 | Lefebvre et al. |
| 5,403,136 A | 4/1995 | Mathys et al. |
| 5,403,317 A | 4/1995 | Bonutti |
| 5,423,850 A | 6/1995 | Berger |
| 5,431,671 A | 7/1995 | Nallakrishnan |
| 5,445,639 A | 8/1995 | Kuslich et al. |
| 5,480,400 A | 1/1996 | Berger |
| 5,490,859 A | 2/1996 | Mische et al. |
| 5,514,137 A | 5/1996 | Coutts |
| 5,527,311 A | 6/1996 | Procter et al. |
| 5,540,707 A | 7/1996 | Ressemann et al. |
| 5,549,612 A | 8/1996 | Yapp et al. |
| 5,549,679 A * | 8/1996 | Kuslich ............ 623/17.12 |
| 5,556,429 A | 9/1996 | Felt |
| 5,562,672 A | 10/1996 | Huebner et al. |
| 5,571,189 A | 11/1996 | Kuslich |
| 5,591,170 A | 1/1997 | Spievack et al. |
| 5,601,553 A | 2/1997 | Trebing et al. |
| 5,607,426 A | 3/1997 | Ralph et al. |
| 5,613,967 A | 3/1997 | Engelhardt et al. |
| 5,616,144 A | 4/1997 | Yapp et al. |
| 5,658,310 A | 8/1997 | Berger |
| 5,665,110 A | 9/1997 | Chervitz et al. |
| 5,674,296 A | 10/1997 | Bryan et al. |
| 5,681,310 A | 10/1997 | Yuan et al. |
| 5,681,311 A | 10/1997 | Foley et al. |
| 5,693,011 A | 12/1997 | Onik |
| 5,695,513 A | 12/1997 | Johnson et al. |
| 5,709,686 A | 1/1998 | Talos et al. |
| 5,720,749 A | 2/1998 | Rupp |
| 5,733,287 A | 3/1998 | Tepic et al. |
| 5,735,853 A | 4/1998 | Olerud et al. |
| 5,766,176 A | 6/1998 | Duncan |
| 5,772,662 A | 6/1998 | Chapman et al. |
| 5,800,433 A | 9/1998 | Benzel et al. |
| 5,807,396 A | 9/1998 | Raveh et al. |
| 5,827,289 A | 10/1998 | Reiley et al. |
| 5,843,103 A | 12/1998 | Wulfman |
| 5,871,486 A | 2/1999 | Huebner et al. |
| 5,888,220 A | 3/1999 | Felt et al. |
| 5,891,145 A | 4/1999 | Morrison et al. |
| 5,904,683 A | 5/1999 | Pohndorf et al. |
| 5,925,056 A | 7/1999 | Thomas et al. |
| 5,928,239 A | 7/1999 | Mirza |
| 5,935,131 A | 8/1999 | Bonutti |
| 5,964,762 A | 10/1999 | Biedermann et al. |
| 5,972,015 A | 10/1999 | Scribner et al. |
| 5,990,194 A | 11/1999 | Dunn et al. |
| 6,017,345 A | 1/2000 | Richelsoph |
| 6,019,776 A | 2/2000 | Preissman et al. |
| 6,022,350 A | 2/2000 | Ganem et al. |
| 6,030,389 A | 2/2000 | Wagner et al. |
| 6,033,411 A | 3/2000 | Preissman |
| 6,048,343 A | 4/2000 | Mathis et al. |
| 6,048,346 A | 4/2000 | Reiley et al. |
| 6,066,154 A | 5/2000 | Reiley et al. |
| 6,071,284 A | 6/2000 | Fox |
| 6,083,672 A | 7/2000 | Roefs et al. |
| 6,096,054 A | 8/2000 | Wyzgala et al. |
| 6,127,597 A | 10/2000 | Beyar et al. |
| 6,139,509 A | 10/2000 | Yuan et al. |
| 6,140,452 A | 10/2000 | Felt et al. |
| 6,171,312 B1 | 1/2001 | Beaty |
| 6,210,376 B1 | 4/2001 | Grayson |
| 6,214,012 B1 | 4/2001 | Karpman et al. |
| 6,221,029 B1 | 4/2001 | Mathis et al. |
| 6,224,604 B1 | 5/2001 | Suddaby |
| 6,231,615 B1 | 5/2001 | Preissman |
| 6,235,043 B1 | 5/2001 | Reiley et al. |
| 6,238,391 B1 | 5/2001 | Olsen et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,264,659 B1 | 7/2001 | Ross et al. |
| 6,273,916 B1 | 8/2001 | Murphy |
| 6,280,456 B1 | 8/2001 | Scribner et al. |
| 6,283,971 B1 | 9/2001 | Temeles |
| 6,296,639 B1 | 10/2001 | Truckai et al. |
| 6,309,420 B1 | 10/2001 | Preissman |
| 6,325,806 B1 | 12/2001 | Fox |
| 6,348,055 B1 | 2/2002 | Preissman |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,423,083 B2 | 7/2002 | Reiley et al. |
| 6,425,887 B1 | 7/2002 | McGuckin et al. |
| 6,425,923 B1 | 7/2002 | Stalcup et al. |
| 6,440,138 B1 | 8/2002 | Reiley et al. |
| 6,447,514 B1 | 9/2002 | Stalcup et al. |
| 6,450,973 B1 | 9/2002 | Murphy |
| 6,488,667 B1 | 12/2002 | Murphy |
| 6,494,535 B2 | 12/2002 | Galbreath |
| 6,558,386 B1 | 5/2003 | Cragg |
| 6,558,390 B2 | 5/2003 | Cragg |
| 6,558,396 B1 | 5/2003 | Inoue |
| 6,565,572 B2 | 5/2003 | Chappius |
| 6,575,979 B1 | 6/2003 | Cragg |
| 6,582,439 B1 | 6/2003 | Sproul |
| 6,582,446 B1 | 6/2003 | Marchosky |
| 6,592,559 B1 | 7/2003 | Pakter et al. |
| 6,595,998 B2 | 7/2003 | Johnson et al. |
| 6,599,520 B2 | 7/2003 | Scarborough et al. |
| 6,607,544 B1 | 8/2003 | Boucher et al. |
| 6,613,018 B2 | 9/2003 | Bagga et al. |
| 6,613,054 B2 | 9/2003 | Scribner et al. |
| 6,613,089 B1 | 9/2003 | Estes et al. |
| 6,620,162 B2 | 9/2003 | Kuslich et al. |
| 6,626,903 B2 | 9/2003 | McGuckin, Jr. et al. |
| 6,632,235 B2 | 10/2003 | Weikel et al. |
| 6,641,587 B2 | 11/2003 | Scribner et al. |
| 6,645,213 B2 | 11/2003 | Sand et al. |
| 6,652,568 B1 | 11/2003 | Becker et al. |
| 6,663,647 B2 | 12/2003 | Reiley et al. |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,886 B2 | 1/2004 | Weikel et al. |
| 6,685,718 B1 | 2/2004 | Wyzgala et al. |
| 6,689,132 B2 | 2/2004 | Biscup |
| 6,699,242 B2 | 3/2004 | Heggeness |
| 6,706,069 B2 | 3/2004 | Berger |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |

(56) References Cited

U.S. PATENT DOCUMENTS

| | | |
|---|---|---|
| 6,740,093 B2 | 5/2004 | Hochschuler et al. |
| 6,746,451 B2 | 6/2004 | Middleton et al. |
| 6,749,595 B1 | 6/2004 | Murphy |
| 6,752,791 B2 | 6/2004 | Murphy et al. |
| 6,752,809 B2 | 6/2004 | Gorek |
| 6,758,855 B2 | 7/2004 | Fulton, III et al. |
| 6,758,863 B2 | 7/2004 | Estes et al. |
| 6,770,079 B2 | 8/2004 | Bhatnagar et al. |
| 6,780,191 B2 | 8/2004 | Sproul |
| 6,790,210 B1 | 9/2004 | Cragg et al. |
| 6,805,697 B1 | 10/2004 | Helm et al. |
| 6,814,734 B2 | 11/2004 | Chappuis et al. |
| 6,832,988 B2 | 12/2004 | Sproul |
| 6,843,796 B2 | 1/2005 | Harari et al. |
| 6,852,095 B1 | 2/2005 | Ray |
| 6,863,672 B2 | 3/2005 | Reiley et al. |
| 6,863,676 B2 | 3/2005 | Lee et al. |
| 6,869,445 B1 | 3/2005 | Johnson |
| 6,887,246 B2 | 5/2005 | Bhatnagar et al. |
| 6,899,716 B2 | 5/2005 | Cragg |
| 6,902,547 B2 | 6/2005 | Aves et al. |
| 6,916,308 B2 | 7/2005 | Dixon et al. |
| 6,921,403 B2 | 7/2005 | Cragg et al. |
| 6,923,813 B2 | 8/2005 | Phillips et al. |
| 6,932,843 B2 | 8/2005 | Smith et al. |
| 6,939,351 B2 | 9/2005 | Eckman |
| 6,960,215 B2 | 11/2005 | Olson, Jr. et al. |
| 6,960,900 B2 | 11/2005 | Fogarty et al. |
| 6,979,341 B2 | 12/2005 | Scribner et al. |
| 6,979,352 B2 | 12/2005 | Reynolds |
| 6,981,981 B2 | 1/2006 | Reiley et al. |
| 6,984,063 B2 | 1/2006 | Barker et al. |
| 7,001,342 B2 | 2/2006 | Faciszewski |
| 7,008,433 B2 | 3/2006 | Voellmicke et al. |
| 7,014,633 B2 | 3/2006 | Cragg |
| 7,044,954 B2 | 5/2006 | Reiley et al. |
| 7,056,321 B2 | 6/2006 | Pagliuca et al. |
| 7,077,865 B2 | 7/2006 | Bao et al. |
| 7,087,058 B2 | 8/2006 | Cragg |
| 7,114,501 B2 | 10/2006 | Johnson et al. |
| 7,144,397 B2 | 12/2006 | Lambrecht et al. |
| 7,153,305 B2 | 12/2006 | Johnson et al. |
| 7,153,307 B2 | 12/2006 | Scribner et al. |
| 7,156,860 B2 | 1/2007 | Wallsten |
| 7,156,861 B2 | 1/2007 | Scribner et al. |
| 7,160,306 B2 | 1/2007 | Matsuzaki et al. |
| 7,226,481 B2 | 6/2007 | Kuslich |
| 7,234,468 B2 | 6/2007 | Johnson et al. |
| 7,238,209 B2 | 7/2007 | Matsuzaki et al. |
| 7,241,297 B2 | 7/2007 | Shaolian et al. |
| 7,241,303 B2 | 7/2007 | Reiss et al. |
| 7,252,671 B2 | 8/2007 | Scribner et al. |
| 7,252,686 B2 | 8/2007 | Carrison et al. |
| 7,295,868 B2 | 11/2007 | Bascle et al. |
| 7,295,869 B2 | 11/2007 | Bascle et al. |
| 7,309,338 B2 | 12/2007 | Cragg |
| 7,318,826 B2 | 1/2008 | Teitelbaum et al. |
| 7,326,203 B2 | 2/2008 | Papineau et al. |
| 7,329,259 B2 | 2/2008 | Cragg |
| 7,346,385 B2 | 3/2008 | Bascle et al. |
| 7,399,739 B2 | 7/2008 | Shimp |
| 7,473,256 B2 | 1/2009 | Assell et al. |
| 7,476,226 B2 | 1/2009 | Weikel et al. |
| 7,488,320 B2 | 2/2009 | Middleton |
| 7,488,377 B2 | 2/2009 | Schroeter |
| 7,491,236 B2 | 2/2009 | Cragg et al. |
| 7,500,977 B2 | 3/2009 | Assell et al. |
| 7,510,579 B2 | 3/2009 | Preissman |
| 7,530,993 B2 | 5/2009 | Assell et al. |
| 7,534,245 B2 | 5/2009 | Chappuis |
| 7,534,256 B2 | 5/2009 | Cragg |
| 7,540,875 B2 | 6/2009 | Jessen |
| 7,544,196 B2 | 6/2009 | Bagga et al. |
| 7,547,324 B2 | 6/2009 | Cragg et al. |
| 7,553,659 B2 | 6/2009 | Brodeur et al. |
| 7,555,343 B2 | 6/2009 | Bleich |
| 7,569,056 B2 | 8/2009 | Cragg et al. |
| 7,572,263 B2 | 8/2009 | Preissman |
| 7,588,574 B2 | 9/2009 | Assell et al. |
| 7,608,077 B2 | 10/2009 | Cragg et al. |
| 7,637,872 B1 | 12/2009 | Fox |
| 7,662,173 B2 | 2/2010 | Cragg et al. |
| 7,717,958 B2 | 5/2010 | Cragg et al. |
| 7,740,633 B2 | 6/2010 | Assell et al. |
| 7,753,872 B2 | 7/2010 | Cragg et al. |
| 2001/0010431 A1 | 8/2001 | Sasaki et al. |
| 2001/0011174 A1 | 8/2001 | Reiley et al. |
| 2001/0012968 A1 | 8/2001 | Preissman |
| 2001/0021852 A1 | 9/2001 | Chappius |
| 2001/0041896 A1 | 11/2001 | Reiley et al. |
| 2001/0044626 A1 | 11/2001 | Reiley et al. |
| 2001/0049527 A1 | 12/2001 | Cragg |
| 2002/0016583 A1 | 2/2002 | Cragg |
| 2002/0016593 A1 | 2/2002 | Hearn et al. |
| 2002/0022856 A1 | 2/2002 | Johnson et al. |
| 2002/0026195 A1 | 2/2002 | Layne et al. |
| 2002/0026197 A1* | 2/2002 | Foley et al. ............... 606/105 |
| 2002/0029047 A1 | 3/2002 | Bascle et al. |
| 2002/0032444 A1 | 3/2002 | Mische |
| 2002/0068974 A1 | 6/2002 | Kuslich et al. |
| 2002/0116064 A1 | 8/2002 | Middleton |
| 2002/0156482 A1 | 10/2002 | Scribner et al. |
| 2002/0173796 A1 | 11/2002 | Cragg |
| 2002/0183758 A1* | 12/2002 | Middleton et al. ............ 606/79 |
| 2002/0188300 A1 | 12/2002 | Arramon et al. |
| 2003/0009208 A1 | 1/2003 | Snyder et al. |
| 2003/0032929 A1 | 2/2003 | McGuckin |
| 2003/0032963 A1 | 2/2003 | Reiss et al. |
| 2003/0073998 A1 | 4/2003 | Pagliuca et al. |
| 2003/0074075 A1 | 4/2003 | Thomas et al. |
| 2003/0105469 A1 | 6/2003 | Karmon |
| 2003/0109883 A1 | 6/2003 | Matsuzaki et al. |
| 2003/0130664 A1 | 7/2003 | Boucher et al. |
| 2003/0135237 A1 | 7/2003 | Cragg et al. |
| 2003/0158557 A1 | 8/2003 | Cragg et al. |
| 2003/0171812 A1 | 9/2003 | Grunberg et al. |
| 2003/0191474 A1 | 10/2003 | Cragg et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195628 A1* | 10/2003 | Bao et al. ............... 623/17.12 |
| 2003/0204189 A1 | 10/2003 | Cragg |
| 2003/0220648 A1 | 11/2003 | Osorio et al. |
| 2003/0229353 A1 | 12/2003 | Cragg |
| 2003/0229372 A1 | 12/2003 | Reiley et al. |
| 2003/0233096 A1 | 12/2003 | Osorio et al. |
| 2004/0010260 A1 | 1/2004 | Scribner et al. |
| 2004/0010263 A1 | 1/2004 | Boucher et al. |
| 2004/0010314 A1 | 1/2004 | Matsuzaki et al. |
| 2004/0019354 A1 | 1/2004 | Johnson et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0029248 A1 | 2/2004 | Brodeur et al. |
| 2004/0039406 A1 | 2/2004 | Jessen |
| 2004/0049202 A1 | 3/2004 | Berger |
| 2004/0049203 A1 | 3/2004 | Scribner et al. |
| 2004/0059417 A1 | 3/2004 | Smith et al. |
| 2004/0064144 A1 | 4/2004 | Johnson et al. |
| 2004/0068242 A1 | 4/2004 | McGuckin |
| 2004/0073139 A1 | 4/2004 | Hirsch et al. |
| 2004/0073308 A1 | 4/2004 | Kuslich et al. |
| 2004/0087956 A1 | 5/2004 | Weikel et al. |
| 2004/0092933 A1 | 5/2004 | Shaolian et al. |
| 2004/0097930 A1 | 5/2004 | Justis et al. |
| 2004/0098015 A1 | 5/2004 | Weikel et al. |
| 2004/0098017 A1 | 5/2004 | Saab et al. |
| 2004/0102774 A1 | 5/2004 | Trieu |
| 2004/0122438 A1 | 6/2004 | Abrams |
| 2004/0153064 A1 | 8/2004 | Foley et al. |
| 2004/0153114 A1 | 8/2004 | Reiley et al. |
| 2004/0153115 A1 | 8/2004 | Reiley et al. |
| 2004/0167532 A1 | 8/2004 | Olson et al. |
| 2004/0167561 A1 | 8/2004 | Boucher et al. |

(56) References Cited

U.S. PATENT DOCUMENTS

| | | |
|---|---|---|
| 2004/0167562 A1 | 8/2004 | Osorio et al. |
| 2004/0210231 A1 | 10/2004 | Boucher et al. |
| 2004/0210297 A1 | 10/2004 | Lin et al. |
| 2004/0215197 A1 | 10/2004 | Smith et al. |
| 2004/0215343 A1 | 10/2004 | Hochschuler et al. |
| 2004/0215344 A1 | 10/2004 | Hochschuler et al. |
| 2004/0220577 A1 | 11/2004 | Cragg et al. |
| 2004/0220580 A1 | 11/2004 | Johnson et al. |
| 2004/0225296 A1 | 11/2004 | Reiss et al. |
| 2004/0267269 A1 | 12/2004 | Middleton et al. |
| 2005/0015148 A1 | 1/2005 | Jansen et al. |
| 2005/0038439 A1 | 2/2005 | Eckman |
| 2005/0038514 A1 | 2/2005 | Helm et al. |
| 2005/0038517 A1 | 2/2005 | Carrison et al. |
| 2005/0043737 A1 | 2/2005 | Reiley et al. |
| 2005/0055097 A1 | 3/2005 | Grunberg et al. |
| 2005/0070908 A1 | 3/2005 | Cragg |
| 2005/0090852 A1 | 4/2005 | Layne et al. |
| 2005/0113838 A1 | 5/2005 | Phillips et al. |
| 2005/0113919 A1 | 5/2005 | Cragg et al. |
| 2005/0113928 A1 | 5/2005 | Cragg et al. |
| 2005/0113929 A1 | 5/2005 | Cragg et al. |
| 2005/0119662 A1 | 6/2005 | Reiley et al. |
| 2005/0124989 A1 | 6/2005 | Suddaby |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131529 A1 | 6/2005 | Cragg |
| 2005/0137601 A1 | 6/2005 | Assell et al. |
| 2005/0137602 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0137612 A1 | 6/2005 | Assell et al. |
| 2005/0149034 A1 | 7/2005 | Assell et al. |
| 2005/0149049 A1 | 7/2005 | Assell et al. |
| 2005/0149191 A1 | 7/2005 | Cragg et al. |
| 2005/0165406 A1 | 7/2005 | Assell et al. |
| 2005/0182413 A1 | 8/2005 | Johnson et al. |
| 2005/0182417 A1 | 8/2005 | Pagano |
| 2005/0187556 A1 | 8/2005 | Stack et al. |
| 2005/0203527 A1 | 9/2005 | Carrison et al. |
| 2005/0261695 A1 | 11/2005 | Cragg et al. |
| 2006/0004369 A1 | 1/2006 | Patel et al. |
| 2006/0116689 A1 | 6/2006 | Albans et al. |
| 2006/0116690 A1 | 6/2006 | Pagano |
| 2006/0142795 A1 | 6/2006 | Nguyen et al. |
| 2006/0149268 A1 | 7/2006 | Truckai et al. |
| 2006/0155289 A1 | 7/2006 | Windhager et al. |
| 2006/0235451 A1 | 10/2006 | Schomer et al. |
| 2007/0027464 A1 | 2/2007 | Way et al. |
| 2007/0055259 A1 | 3/2007 | Norton et al. |
| 2007/0123877 A1 | 5/2007 | Goldin et al. |
| 2008/0114364 A1 | 5/2008 | Goldin et al. |
| 2008/0294166 A1 | 11/2008 | Goldin et al. |
| 2008/0294167 A1 | 11/2008 | Schumacher et al. |
| 2009/0131952 A1 | 5/2009 | Schumacher et al. |
| 2010/0241123 A1 | 9/2010 | Middleton et al. |

FOREIGN PATENT DOCUMENTS

| | | |
|---|---|---|
| EP | 0442137 B1 | 8/1991 |
| EP | 0748615 A1 | 12/1996 |
| WO | WO-9007304 A1 | 7/1990 |
| WO | WO-9851226 A2 | 11/1998 |
| WO | WO-9851226 A3 | 11/1998 |
| WO | WO-2004049961 A1 | 6/2004 |

OTHER PUBLICATIONS

European Search Report dated Jun. 11, 2010 for Application No. EP 10002071.8.
International Search Report and Opinion for PCT/US2006/044340 dated Oct. 22, 2007.
International Search Report and Written Opinion for PCT/US2008/064312 dated Jun. 10, 2009.
International Search Report for PCT/US2006/044443 dated Mar. 21, 2007.
Office Action dated Jan. 11, 2008 for U.S. Appl. No. 10/818,452.
Office Action dated Jun. 11, 2007 for U.S. Appl. No. 10/818,452.
Office Action dated Jun. 3, 2003 for U.S. Appl. No. 09/872,042.
Office Action dated Aug. 19, 2010 for U.S. Appl. No. 10/818,452.
Office Action dated Aug. 28, 2002 for U.S. Appl. No. 09/872,042.
Office Action dated Sep. 2, 2010 for U.S. Appl. No. 11/600,313.
Office Action dated Oct. 20, 2008 for U.S. Appl. No. 10/818,452.
Office Action dated Nov. 16, 2009 for U.S. Appl. No. 11/600,313.
Office Action dated Nov. 29, 2006 for U.S. Appl. No. 10/818,452.
Office Action dated Dec. 7, 2009 for U.S. Appl. No. 10/818,452.
Office Action dated Apr. 13, 2006 for U.S. Appl. No. 10/818,452.
Office Action dated Aug. 20, 2009 for U.S. Appl. No. 11/600,313.
U.S. Appl. No. 60/336,557, Middleton, filed Nov. 1, 2001.
Phillips, Frank M., "Minimally Invasive Treatments of Osteoporotic Vertebral Compression Fractures," Spine, vol. 28, No. 15S, 2003, pp. S45-S53.

* cited by examiner

DETAIL Y

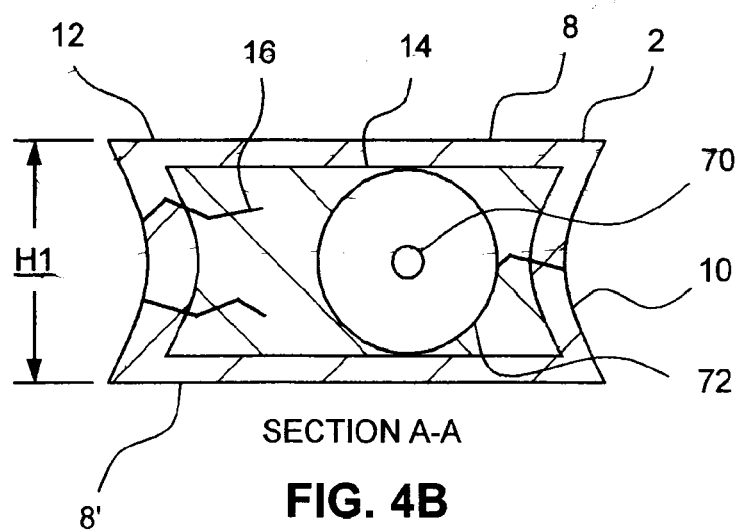
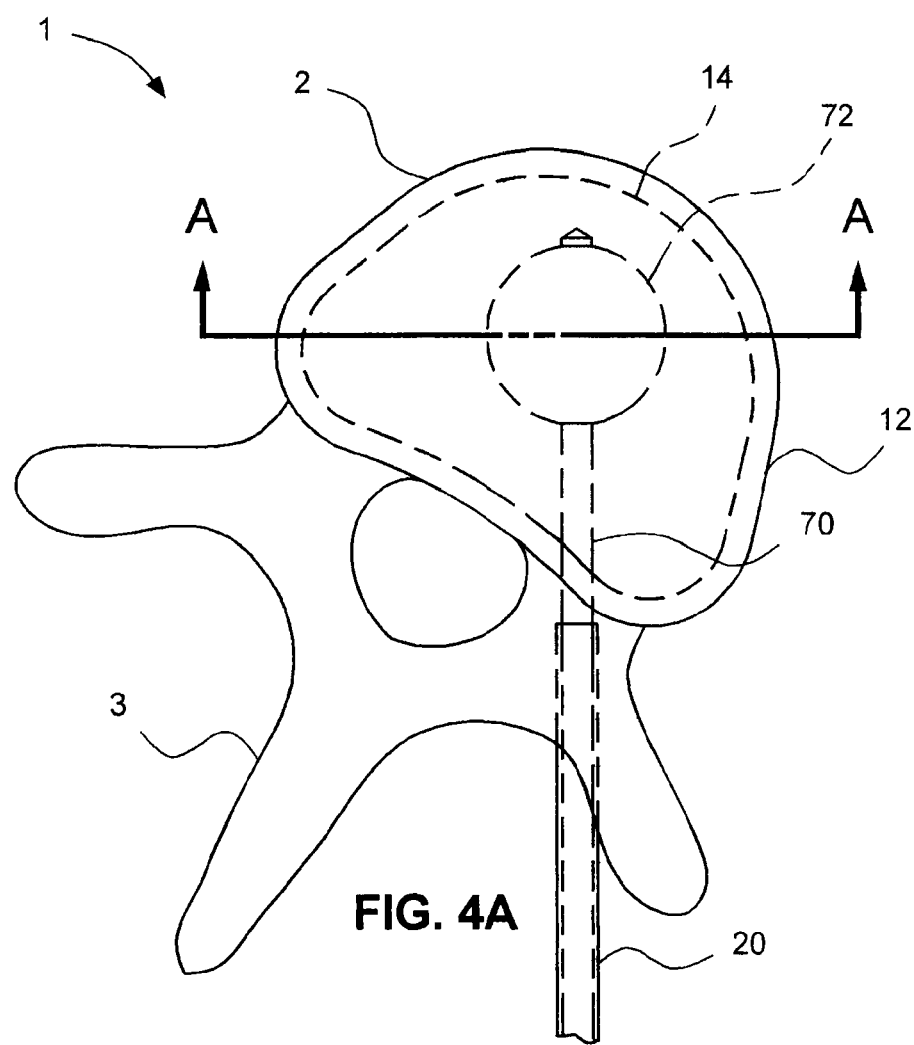

SECTION A-A

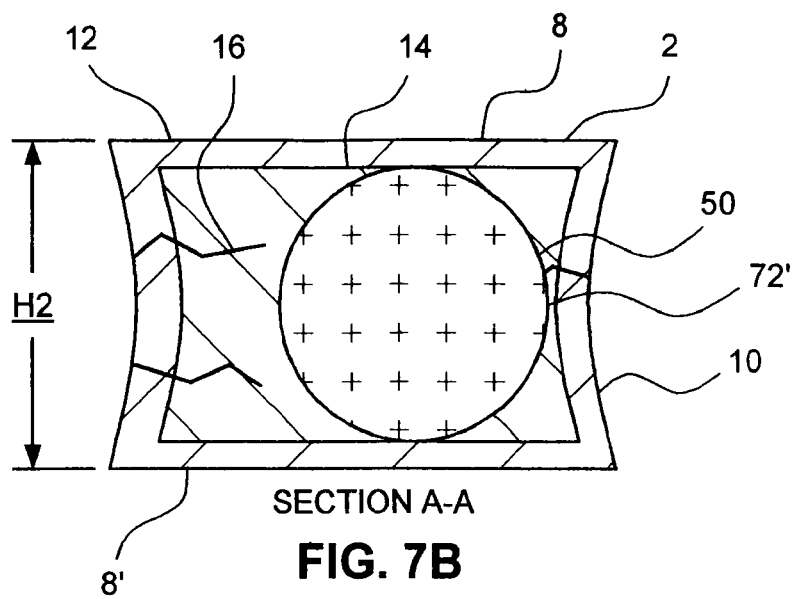
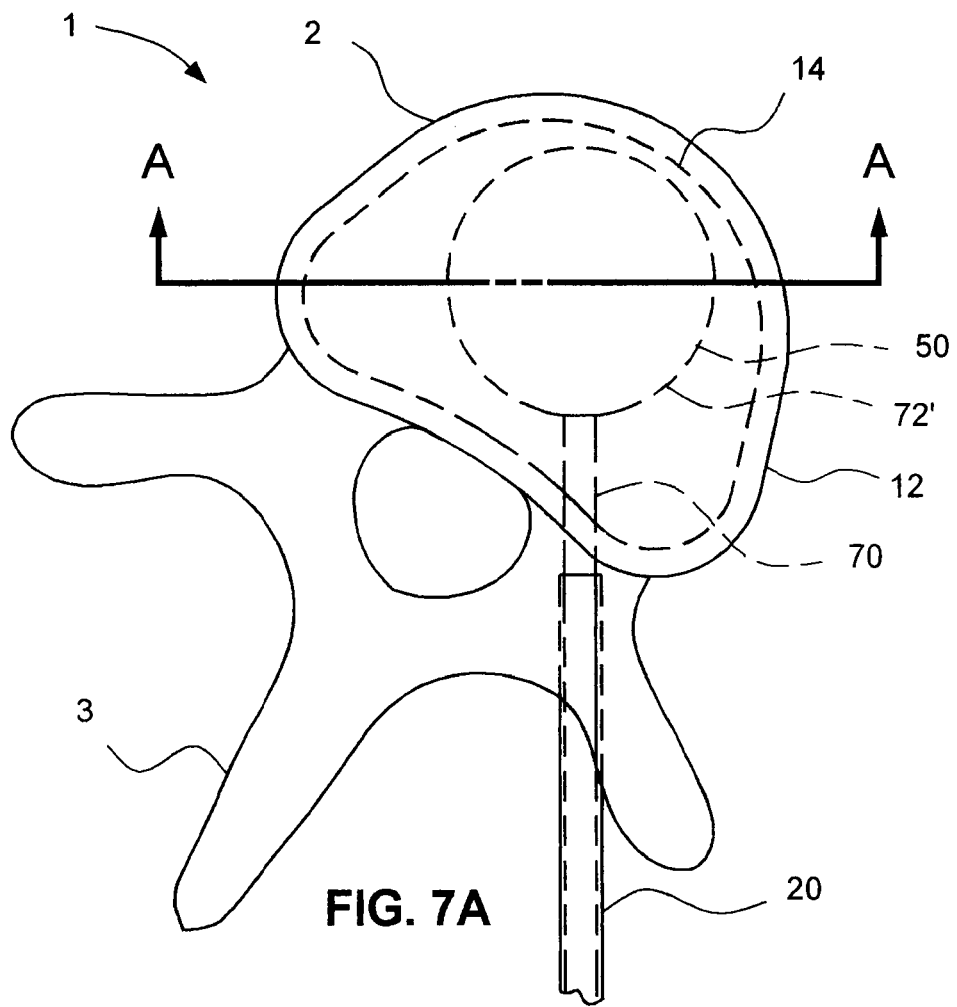

INSTRUMENTS AND METHODS FOR REDUCING AND STABILIZING BONE FRACTURES

CROSS-REFERENCE TO RELATED APPLICATIONS

This application is a continuation of U.S. patent application Ser. No. 11/140,413 filed May 27, 2005, which claims the benefit of U.S. Provisional Patent Application No. 60/575,635 filed May 28, 2004. The entirety of both patent applications are hereby incorporated by reference to the fullest extent allowable.

BACKGROUND

The invention described generally relates to instruments and methods for application with skeletal disorders, and, in particular relates to instruments and methods for the reduction and stabilization of skeletal fractures.

Fracture reduction and/or stabilization are generally practiced to substantially restore or repair skeletal structures to their pre-fractured state. In practice, materials, such as in-situ curable materials (e.g., bone cements) and/or implants are often used to help stabilize fractured bone. In one clinical procedure known as vertebroplasty, bone cement is injected into a fractured vertebral body to stabilize bone fragments. This and other procedures may also additionally use one or a number of devices for reduction and stabilization of a fracture. For vertebroplasty, a device is used to assist in the formation of a cavity in the vertebra prior to injection of the in-situ curable material. Another device used with some procedures is a bone tamp used to reduce the fracture.

SUMMARY

The present invention solves many problems associated with current methods and devices for reduction, stabilization, restoration, and repair of skeletal fractures.

Generally, and in one form described herein are methods of reducing and/or stabilizing a fracture in bone. The method includes cutting a portion of the bone having a fracture to create a cavity. The cavity may be substantially axisymmetric and may be cut using any suitable device, such as a tissue cavitation device. The cavity is then expanded to reduce the fracture. A suitable expanding device includes a medical balloon as an example. The expanding device is typically positioned proximate to cortical bone. The fracture may be further reduced by filling the cavity with a material. The material may fully or partially fill the cavity. Examples of suitable materials include implants and in-situ materials that are curable or hardenable. Such materials may be permanent, resorbable, penetrating and combinations thereof. The material filling the cavity offers stabilization to the fracture. Any bone fragments near the fracture may also be stabilized. When suitable, the cutting of a portion of the bone having a fracture is preceded by the formation of at least one passage to the fracture site. Depending on the type of bone having the fracture, the passage(s) may be intracortical, extracortical, intrapedicular, extrapedicular, and combinations thereof.

Additionally, described herein is a method for treating bone comprising the steps of: forming a passage in a vertebra; forming a cavity in the vertebra, wherein the cavity at least extends radially from the passage, wherein the cavity has a first size and a first portion of the cavity is proximate to a vertebral endplate; providing an inflatable device configured for expansion; introducing the inflatable device configured for expansion into the cavity; and expanding the inflatable device configured for expansion to provide an expansion force sufficient to enlarge the cavity to a second size. The expansion force may be provided proximate to the vertebral endplate, comprising a first endplate and a second endplate. The expansion force may be provided to reduce a vertebral compression fracture. The first endplate may be a superior endplate and the second endplate may be an inferior endplate. Forming the cavity comprises a method of cutting bone, the method of cutting bone selected from the group consisting of shearing, cutting, scraping, and combinations thereof. The inflatable device may be a balloon. The inflatable device may be non-compliant. The inflatable device may be semi-compliant. The inflatable device may be configured to manipulate cortical bone to reduce a fracture. The method may further comprise filling the cavity with a material after expanding the inflatable device, the material selected from the group consisting of implantable material, in-situ curable material, in-situ hardenable material, permanent material, resorbable material, penetrating material, and combinations thereof. The passage in the vertebra may comprise forming an entry hole from which the cavity is formed. Forming the cavity may further comprise cutting bone. The cavity may be substantially axisymmetric. The cavity may be substantially non-axisymmetric. In one form, the second size of the cavity has an increased volume as compared with a volume associated with the first size of the cavity. Forming the passage in the vertebra may precede forming the cavity. Forming the passage in the vertebra may occur substantially concomitantly with forming the cavity.

Still further, described herein is a method for treating bone comprising the steps of: forming a passage in a vertebra along a linear axis; providing a tissue cavitation device; forming a cavity in the vertebra with the tissue cavitation device, wherein the cavity has first volume that extends from the passage proximate to a first vertebral endplate; providing an inflatable device configured for expansion in the cavity; and expanding the inflatable device configured for expansion within the cavity to expand the cavity to a second volume, wherein the second volume is greater than the first volume. The cavity is proximate to a second vertebral endplate. The cavity is proximate to but separated from the first vertebral endplate by a layer of cancellous bone. The cavity has a boundary and a portion of the boundary consists of cortical bone. The cavity has a boundary and a portion of the boundary consists of cancellous bone. The inflatable device configured for expansion is a balloon. In one form, expanding the inflatable device manipulates cortical bone to reduce a fracture. The method may further comprise filling the cavity after expanding with a material, wherein the material is a filling material selected from the group consisting of implant material, in-situ curable material, in-situ hardenable material, permanent material, resorbable material, penetrating material, and combinations thereof. In one form, forming the passage in the vertebra comprises forming an entry hole about which the cavity is formed. Forming the cavity in the vertebra may comprise disrupting bone. The cavity may be substantially axisymmetric. The cavity may be substantially non-axisymmetric. The cavity may be formed with rotational actuation of the tissue cavitation device. Forming the passage in the vertebra may precede forming the cavity. Forming the passage in the vertebra may occur substantially concomitantly with the step of forming the cavity.

Also described herein is a method of treating bone comprising the steps of: forming a passage in a vertebra; providing a tissue cavitation device, inserting the tissue cavitation device into the passage; forming a cavity with the tissue cavitation device along a central portion of the vertebra, wherein the cavity extends proximate to a vertebral body endplate; providing an inflatable device configured for expansion with a working fluid; inserting the inflatable device into the cavity that is the central portion of the vertebra; and expanding the inflatable device to expand the cavity. The cavity may be proximate a first region of the vertebral body endplate which includes cortical bone. The cavity may be proximate a second region of the vertebral body endplate which includes cortical bone, wherein the first region is a superior endplate and the second region is an inferior endplate. The cavity may be proximate a first region of the vertebral body endplate and separated from the first region by a layer of cancellous bone. In one form, the cavity has a boundary, a portion of which is cortical bone. The cavity may also have a boundary, a portion of which is cancellous bone. Forming the cavity may comprise a method of separating bone, the method of separating bone selected from the group consisting of shearing, cutting, scraping, and combinations thereof. The inflatable device may be a balloon. The inflatable device may be substantially non-compliant. The inflatable device may be semi-compliant. The inflatable device may be used to manipulate cortical bone to reduce a fracture. The method may further comprise filling the cavity with a material, wherein the material is a filling material selected from the group consisting of implant material, in-situ curable material, in-situ hardenable material, permanent material, resorbable material, penetrating material, and combinations thereof. The cavity may be substantially axisymmetric. The cavity may be substantially non-axisymmetric. In one form, a working end of the tissue cavitation device is transformable between a first shape for entry into the passage and a second shape for forming the cavity. In one or more embodiments, the tissue cavitation device comprises: a shaft having a diameter and a longitudinal axis; and flexible cutting element associated with the shaft, wherein the flexible cutting element is configured to assume a first shape for insertion and configured to assume a second shape suitable for forming the cavity that has a diameter greater than a diameter of the shaft when the shaft is rotated about the longitudinal axis of the shaft. The cavity is formed with rotational actuation of the tissue cavitation device. Wherein forming the passage in the vertebra may precedes forming the cavity. Wherein forming the passage in the vertebra may occur substantially concomitantly with forming the cavity. In some forms, expanding the inflatable device provides a distraction force.

A method for treating bone is also described that comprises: forming a passage in a vertebra along a linear axis; providing a tissue cavitation device; forming a cavity in the vertebra with the tissue cavitation device by separating bone, wherein the cavity is formed with rotational actuation of the tissue cavitation device, wherein the cavity extends from the passage; providing an inflatable device configured for expansion; and expanding the inflatable device configured for expansion within the cavity to enlarge the cavity.

Those skilled in the art will further appreciate the above-noted features and advantages of the invention together with other important aspects thereof upon reading the detailed description that follows in conjunction with the drawings.

BRIEF DESCRIPTION OF SEVERAL VIEWS OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 4A is a superior view of the bone of FIG. 1 with a fracture site and after performing a step of the present invention;

FIG. 4B is a cross-sectional view of the bone of FIG. 4A showing the step of FIG. 4A and a cavity within the bone;

FIG. 7A is a superior view of the bone of FIG. 5A when performing still another step of the present invention; and FIG. 7B is a cross-sectional view of the bone of FIG. 7A showing the bone with an in-situ material in the cavity.

DETAILED DESCRIPTION

Figure 1:
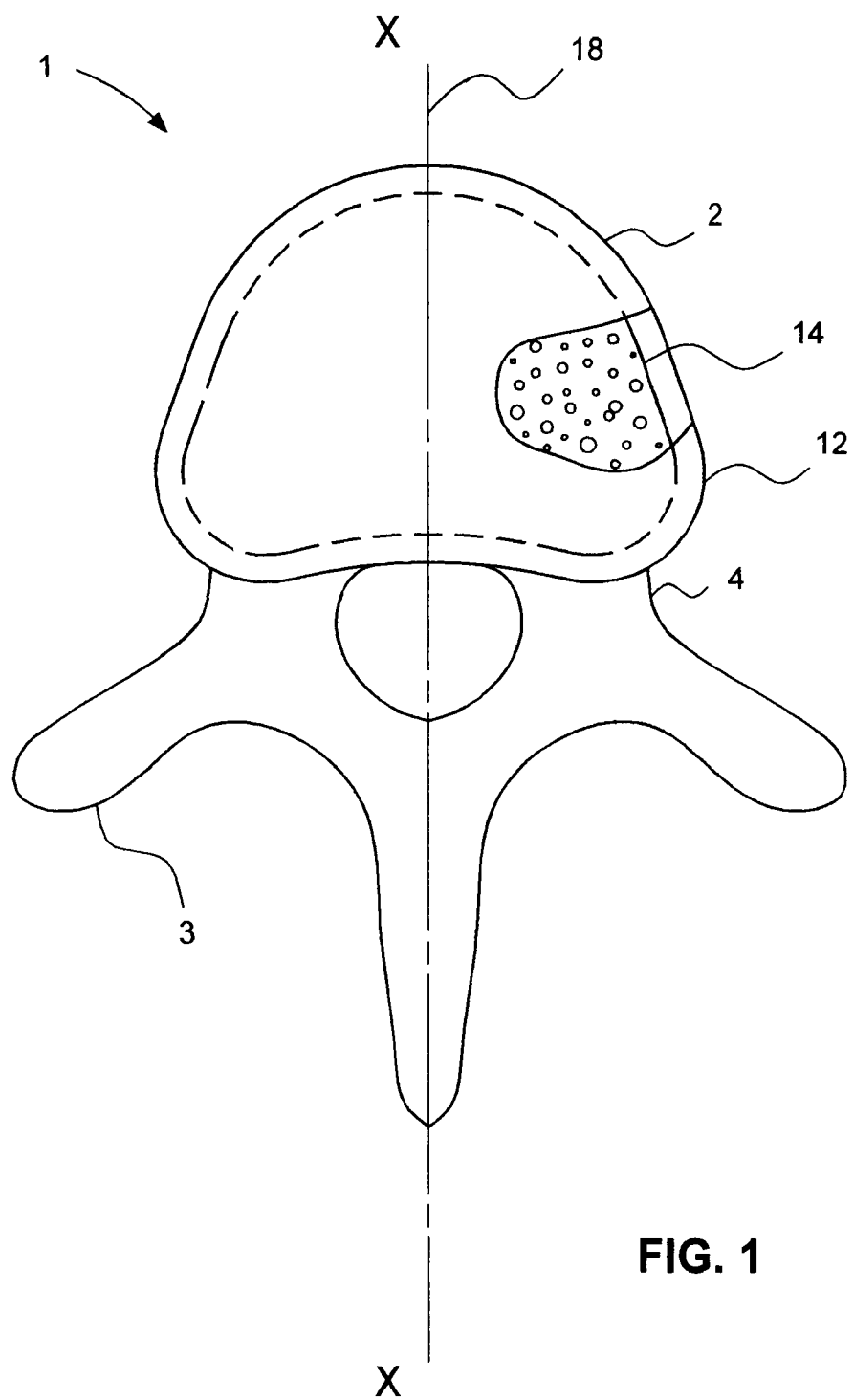
FIG. 1 is a superior view of a human bone.

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

Instruments and methods will be disclosed for reducing and stabilizing bone fractures. The method may be useful for fractured bone, including vertebral bone. Typically, vertebral bone fractures in compression. This type of fracture is most common in the thoracic and/or lumbar regions of the spine and may coincide with regions of osteoporotic bone.

Common medical nomenclature may be used when describing aspects of the present invention. As used herein, superior is nearer the head in relation to a specific reference point, inferior is nearer the feet in relation to a specific reference point, anterior is forward in relation to a specific reference point and posterior is rearward in relation to a specific reference point. The midsagittal plane is an imaginary plane dividing the body into a right side and left side. A frontal plane is any imaginary vertical plane orthogonal to the midsagittal plane.

Referring not to FIG. 1, the figure shows anatomical structures of a human bone. In this example, the bone is vertebra 1 in a superior view. Vertebra 1 is comprised of body 2 and posterior elements 3. Posterior elements 3 include pedicle 4. An edge view of midsagittal reference plane 18 is shown in FIG. 1 as line X-X. Body 2 is generally comprised of two types of bone: cortical bone 12 and cancellous bone 14. In contrast to cortical bone, cancellous bone has a substantial degree of porosity. In addition there are transition regions of varying porosity between cancellous and cortical bone. For the present invention, the bone does not necessarily require all the above-identified elements. For example, some bone do not comprise pedicle 4; other bone may be more symmetrical in shape when shown in superior view. All bone, however, will include a body with some degree of cancellous bone and some degree of cortical bone.

Figure 2B:
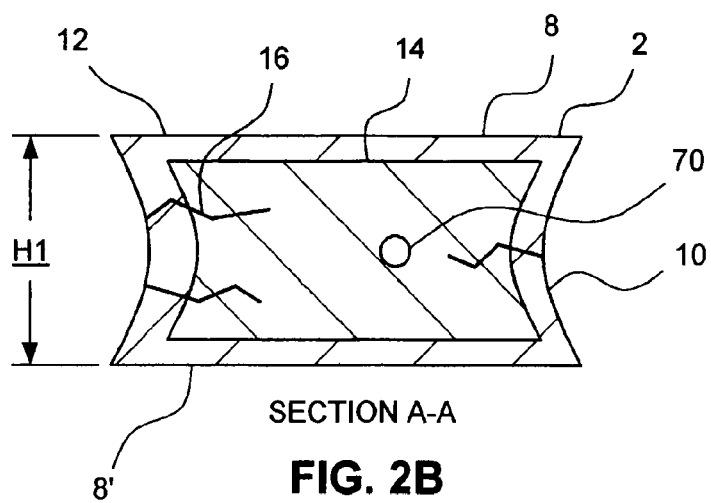
FIG. 2B is a cross-sectional view of the bone in FIG. 2A or FIG. 1 showing a fracture.
Figure 2A:
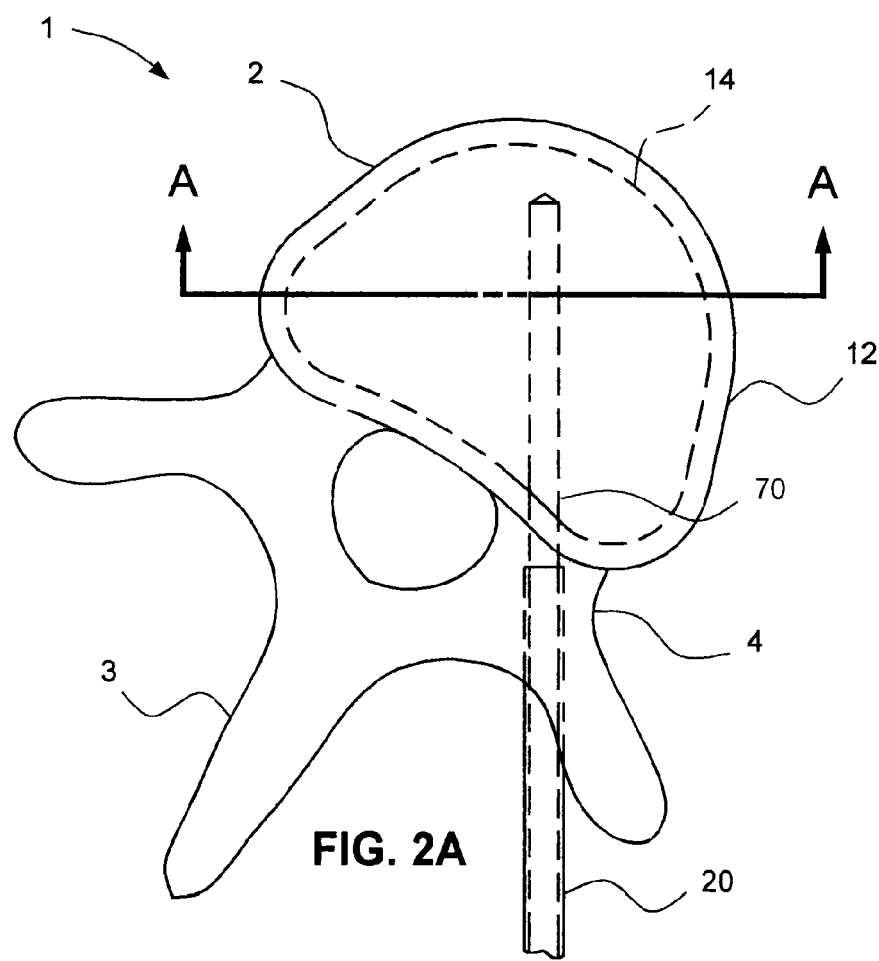
FIG. 2A is another superior view of a human bone showing the bone a working channel.

Vertebral 1 of FIG. 1 is shown in a superior view in FIG. 2A. FIG. 2B shows relevant cortical bone 12 structures including superior endplate 8, inferior endplate 8', and side wall 10. As a possible site of fracture, fracture 16 is shown to include side wall 10 and cancellous bone 14. Fractures may also occur in locations such as superior endplate 8 and inferior endplate 8', as examples.

Continuing to refer to FIG. 2A and FIG. 2B, passage 70 is formed within body 2 using any of a number of methods and surgical instruments known to one of ordinary skill in the art. Examples of possible surgical instruments used to create passage 70 include a bone biopsy needle, guide pin, stylet, stylus, drill-bit instrument, and obturator. Referring again to FIG. 2A, working channel 20 is typically used to pass instruments into and out of body 2. While body 2 will typically have a working channel, the formation of passage 70 may not be essential. In some instances, a drill-bit instrument is used within working channel 20 to create passage 70, wherein the diameter of passage 70 is similar to the inner diameter of working channel 20. Other appropriate instruments may also be used with the working channel. Working channel 20 typically remains in position for additional steps of the present invention. As shown in FIG. 2A, access to body 2 is thru pedicle 4 (intrapedicular); however access may also include one or a number of posterior elements 3 or may be outside pedicle 4 (extrapedicular). The surgical approach typically depends on the site of the fracture, the patient, and/or surgeon preferences.

The term "tissue cavitation device" as used herein will refer to a device useful with the present invention. This device is capable of separating a portion of bone having a fracture and providing a cavity in the portion of the bone including or near the site of the fracture. By use of such a device, the device may separate the bone by cutting, shearing or scraping the bone, as examples. The separation creates a cavity that is typically substantially larger in diameter than the access passage, as shown in FIG. 2A as passage 70. A suitable device and use of such a device is described in U.S. Pat. No. 6,746,451 to Middleton et. al, which is hereby incorporated by reference. The Middleton device is comprised of a rotatable shaft interconnected to a flexible cutting element. The flexible cutting element has a first shape suitable for minimally invasive passage into tissue, and the flexible cutting element has a means to move toward a second shape suitable for forming a cavity in the tissue, such as bone. Several embodiments of the Middleton device may also be adapted to a powered and/or a manual surgical drill, as needed.

Figures 3A, 3B, 3C:
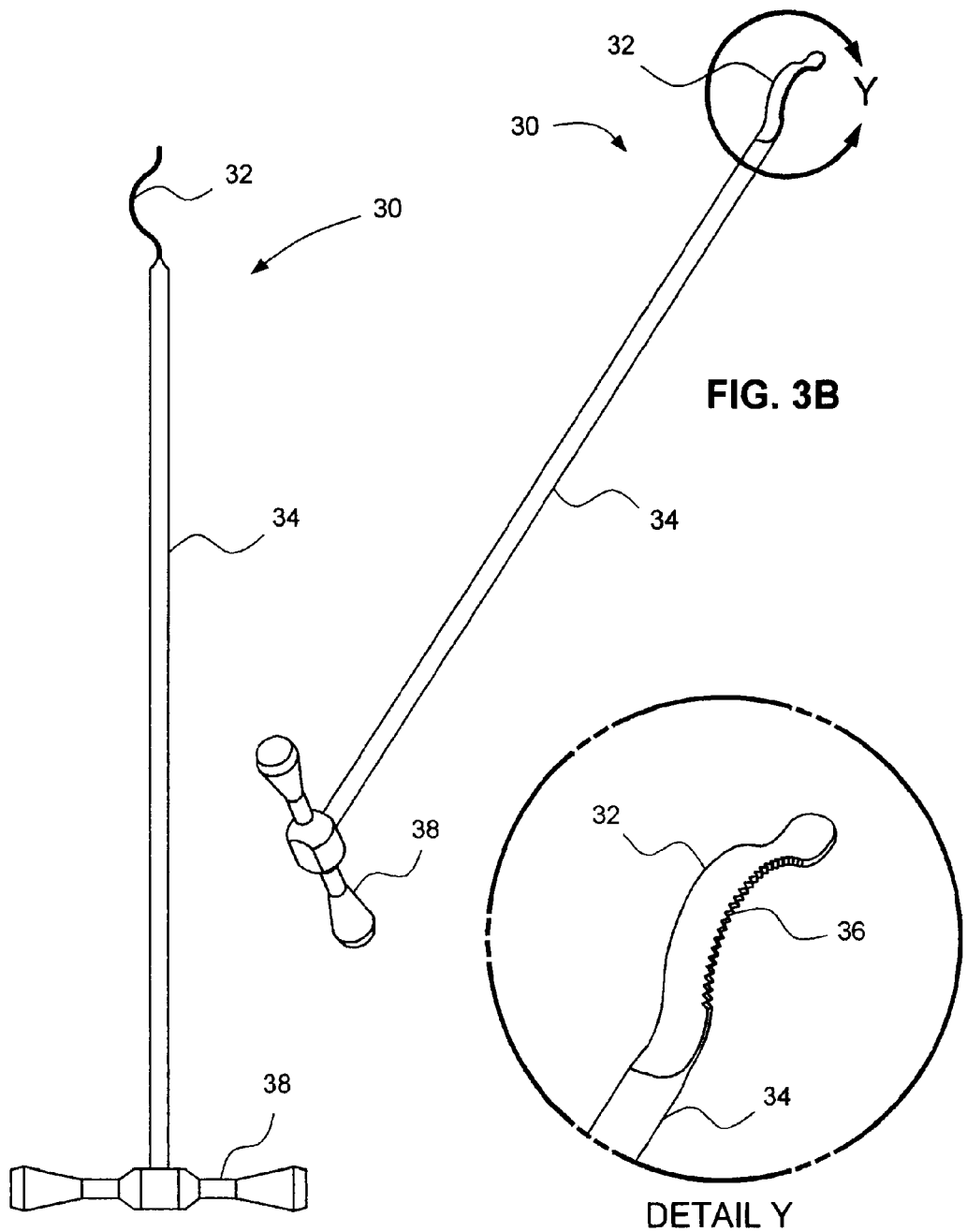
FIG. 3 is a schematic of a device useful with the present invention showing (A) a side view, (B) a perspective view, and (C) a detailed perspective view of a portion of the device.

Referring now to FIG. 3A, FIG. 3B, and FIG. 3C, examples of a suitable device are shown. Device 30 comprises a flexible cutting element 32, a shaft 34, a serration 36, and a T-handle 38. T-handle 38 allows the user (e.g., surgeon) to rotate device 30 during use or in the formation of a cavity.

Referring now to FIG. 4A and FIG. 4B, vertebra 1 is shown with cavity 72 provided after use of a device, such as device 30 shown in FIG. 3. Here, cavity 72 was created by using a device, such as device 30, within passage 70 to cut a portion of the bone, the bone being cancellous bone 14 and/or cortical bone 12. Although passage 70 is useful to position device 30, it is contemplated that a cavity 72 can be made without requiring passage 70. Cavity 72, as shown in FIG. 4A and FIG. 4B, is generally spherical, although other shapes are also contemplated, such as cylindrical and elliptical shapes, as examples. In general, it is desirable to extend the boundary of cavity 72 so that it at least partially includes, or is in proximity of, superior endplate 8 and inferior endplate 8'. Hence, cavity 72 is typically in proximity to cortical bone 12. Accordingly, cavity 72 may be bound, in part, by cortical bone 12. Cavity 72 is initially formed by device 30; in which device 30 cuts, shears, and/or scrapes a portion of bone near the fracture. Cavity 72 is not initially formed by compacting the bone using an expanding device.

Often, it is desirable to have the height and width of cavity 72 be of similar or equal dimensions. Therefore, an axisymmetric shape of cavity 72 is useful, although non-axisymmetric shapes are also contemplated. For example, device 30, shown in FIG. 3, may be designed, through the use of available materials and geometry, to effectively cut cancellous bone but ineffectively cut cortical bone which may lead to a non-axisymmetric bone cavity, despite complete rotation of shaft 34 during use of device 30. Alternatively, both cancellous and cortical bone may be cut by device 30. Thus, the boundaries of the cavity may be cortical and/or cancellous bone. Various elements of the present invention, to include position and size of the bone cavity, will become apparent to one of ordinary skill in the art.

Figure 5B:
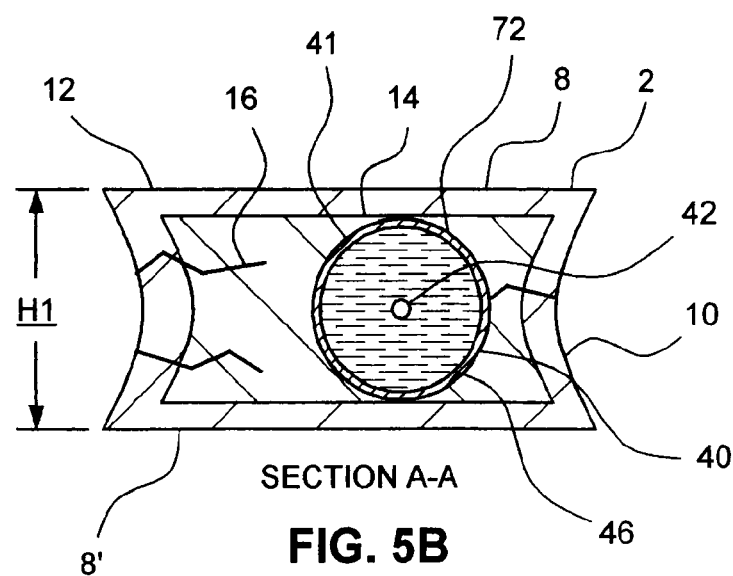
FIG. 5B is a cross-sectional view of the bone of FIG. 5A showing the step of FIG. 5A and an expanding device in the cavity of the bone.
Figure 5A:
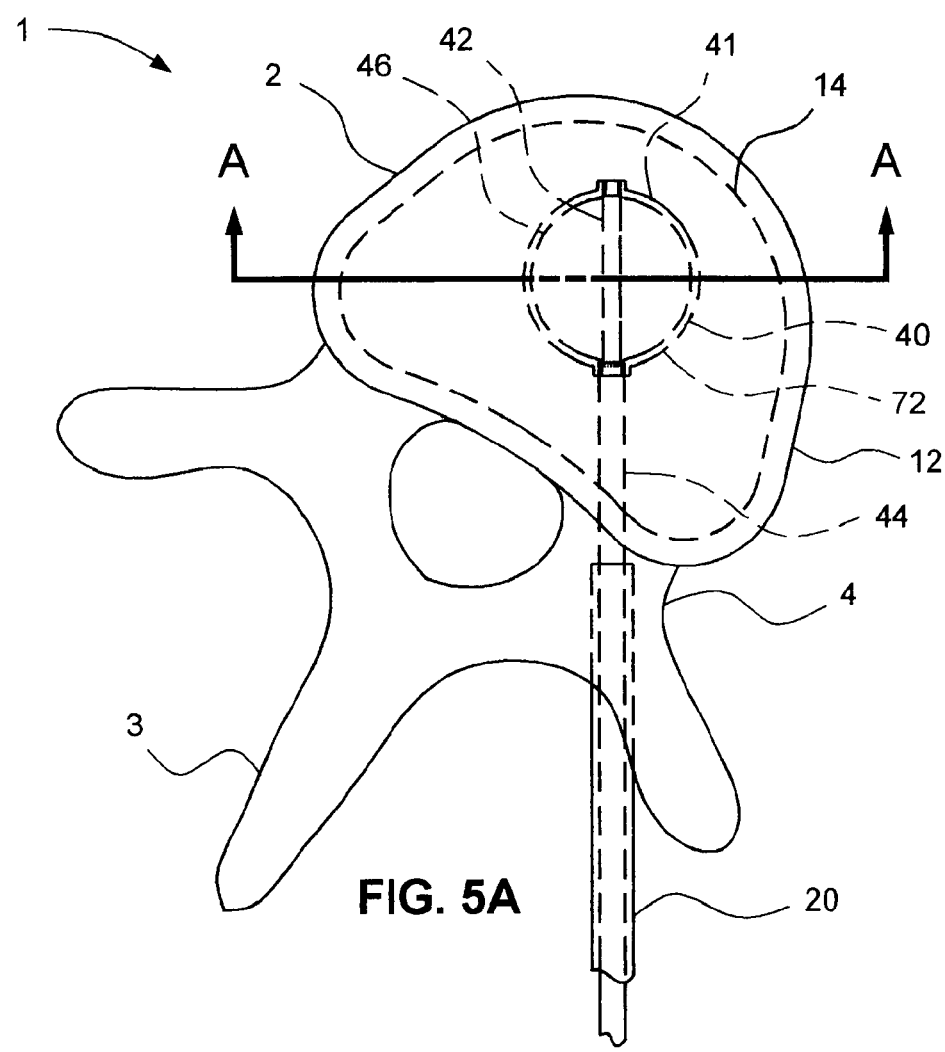
FIG. 5A is a superior view of the bone of FIG. 4A when performing another step of the present invention.

A further step to reduce the fracture includes expansion of the cavity with an expanding device. The expanding device is one that expands the shape of the cavity in at least one dimension. The device, itself may be involved in the expansion. Alternatively, one or more materials may be used with the device for such expansion. Example of expanding devices are a medical balloon or SKy Bone Expander (Disc Orthopaedic Technologies Inc., New Jersey, USA). Other suitable expandable means may also be used. Referring now to FIG. 5A and FIG. 5B, expanding device 40 is positioned within cavity 72. For FIGS. 5A and 5B, expanding device 40 is a medical balloon which is inflated with working substance 46, such as a fluid or saline. Readily available surgical inflation devices, including a syringe and syringe-like devices, are suitable for pressurizing the expanding device. Not every expanding device, however, will require pressurization. Each expanding device will have components and functions known to those skilled in the art. For example, expanding device 40 as shown in FIG. 5A and FIG. 5B, typically comprises an expandable portion 41, inner cannula 42, and outer cannula 44. The expandable portion 41 may be constructed of a number of materials, such as a non-compliant or semi-compliant material (e.g., poly(ethylene terephthalate) or Nylon). For any expanding device, the expanding portion may be resorbable, nonresorbable, porous or nonporous.

In general, because cortical bone is stiffer and stronger as compared with cancellous bone, expanding device 40 may be positioned initially at or in proximity to cortical bone 12. The position of expanding device 40 is typically based on the size, shape, and location of cavity 72. For example, with expanding device 40 as a medical balloon, the top and bottom surface of expandable portion 41 may be initially positioned at or in proximity of cortical bone 12 upon initial pressurization of expandable portion 41. Therefore expandable portion 41 may provide relatively direct distraction forces against superior endplate 8 and inferior endplate 8' upon pressurization of expandable portion 41. The width of expandable portion 41 relates to the vertical distraction forces expandable portion 41 provides for a given pressure. Relative to passage 70, cavity 72 is typically larger, allowing pressurization of a relatively large expandable portion 41. Thus, for a given pressure, a larger expanding expandable portion 41 would generally provide greater distraction forces. Or, for a required distraction force, a larger expanding portion 41 generally requires lower pressure. Typically, a larger expanding device provides greater surface area for distraction and provides broader, more uniform distraction, while avoiding local pressure concentrations. Referring to FIG. 5B, H1 represents the height of body 2 prior to reduction of the fracture. Inflation of expandable portion 41 is intended to reduce the fracture in the form of an increased body height of the bone in at least one dimension.

Figure 6B:
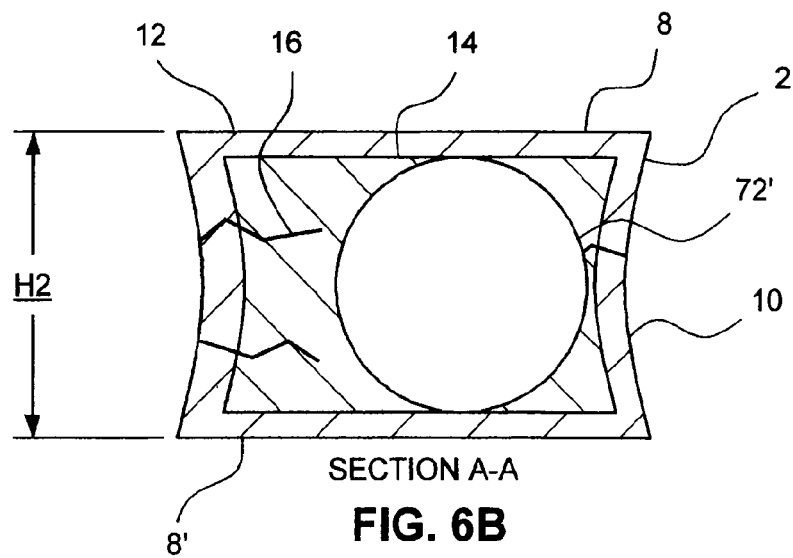
FIG. 6B is a cross-sectional view of the bone of FIG. 6A showing the step of FIG. 6A and a restored bone.
Figure 6A:
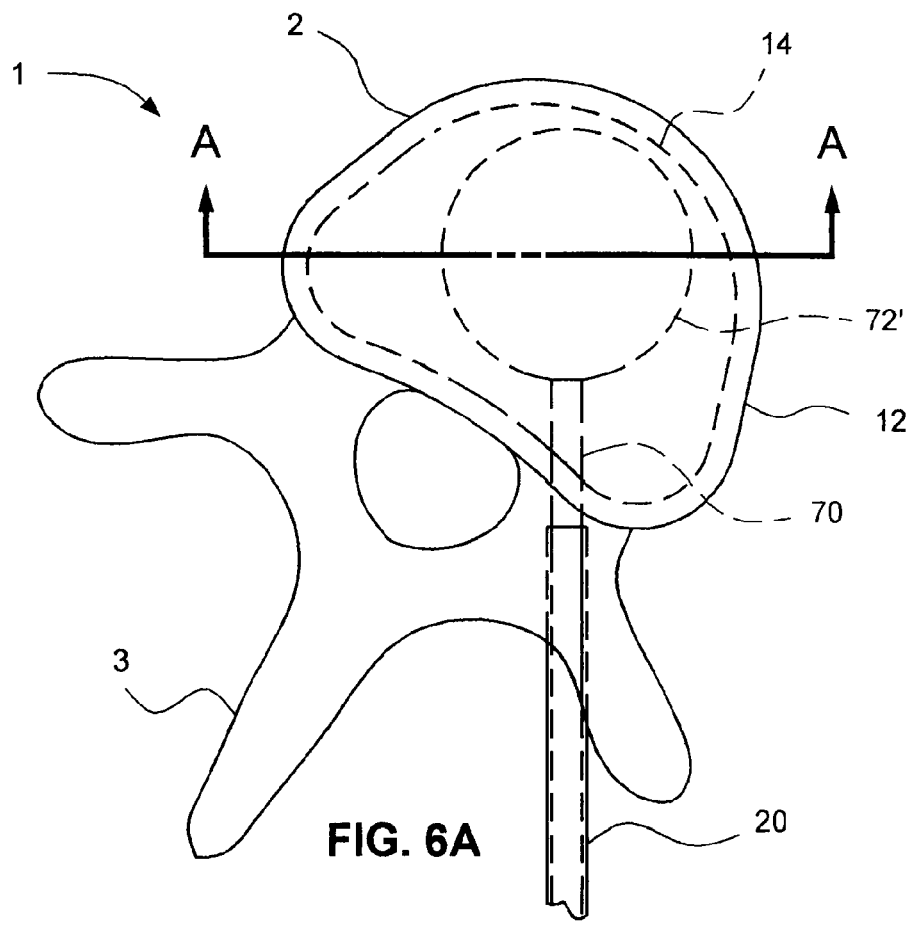
FIG. 6A is a superior view of the bone of FIG. 5A when performing yet another step of the present invention.

Referring now to FIG. 6A and FIG. 6B, body 2 is shown following inflation of expanding device 40 of FIG. 5 and removal of expanding device 40. An expanding device may include an implantable portion subsequently left in the patient to become permanent or later resorbed. In suitable embodiments, an expandable portion of expanding device 40 may remain in cavity 72' and be filled with a material further described below. The material and/or the expandable portion may remain permanently in cavity 72' or be later resorbed.

Referring specifically to FIG. 6B, a new vertebral body height, H2, is established in the cavity, reflecting partial or significant restoration toward the pre-fractured height of body 2. In addition, cavity 72, as initially shown in FIG. 4, is now enlarged or otherwise modified, as represented in FIG. 6A and FIG. 6B by cavity 72'. Cavity 72' may, thus, be associated with a reduction of the fracture. This may include, for example as described above, a change in the spatial relationship between endplate 8 and endplate 8'.

The fracture may be further reduced and/or stabilized by any of a number of means, including introduction of a material. Some examples of suitable materials include an implant, a support, an in situ material that is hardenable or curable, and other equivalents. An example of a material used for further reduction is shown in FIG. 7A and FIG. 7B. Here, cavity 72' is filled with in-situ material 50 to provide stability and strength to body 2. The in-situ material 50 may fully or partially fill the volume of cavity 72', including between any bone fragments and any related fractures, especially fracture fissures interconnected directly to cavity 72'. In-situ curable material 50 may also penetrate the pores of cancellous bone 14. The in-situ material may be a permanent material or may be resorbable. Alternatively, the Suitable in-situ materials that be hardened or curable include polymethylmethacrylate-based bone cements and bone substitute materials, such as calcium sulfate compounds, calcium phosphate compounds, demineralized allografts, hydroxyapetites, carbonated apetites (e.g., Synthes' Norian Bone Void Filler), collagen mixtures, mineral and cytokine mixtures, terpolymer resins, difunctional resins (e.g., Orthovita's CORTOSS®), and combinations thereof, as examples. Any passage to cavity 72 and 72', if present, such as working channel 20 or passage 70, is either filled or allowed to heal. Any components used for the introduction of material 50 (or its equivalents) are similarly removed.

The instruments and methods presented in this disclosure are used as examples of the present invention. Those skilled in the art will be able to develop modifications and variants that do not depart from the spirit and scope of the present invention. Variations include using a porous expanding device. Alternately, an expanding device may be filled with a material (e.g., implant or in-situ material that is curable or hardenable) and subsequently left in the patient to become permanent or later resorbed. It is also understood that the expanding device may be an implant or include an implant and, thus, all or part of the device may remain in cavity 72'. Such implants may be metallic or nonmetallic, coated or noncoated.

Alternate surgical approaches are also within the scope of the present invention. For example the instruments and methods may be used on the right side and left side of a body of a bone, such as in a bipedicular approach for vertebral bone. The present invention is applicable to the reduction and stabilization of any bone or fracture site, including fractured vertebra. Accordingly, the present invention offers restoration and repair of a fractured bone comprising cortical and/or cancellous bone.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A method for treating bone comprising the steps of:
forming a passage in a vertebra;
providing a tissue cavitation device,
inserting the tissue cavitation device into the passage in the vertebra;
forming a cavity with the tissue cavitation device along a central portion of the vertebra, wherein the cavity extends proximate to an endplate of a vertebral body, wherein the cavity is proximate a first region and a second region of the vertebral body, wherein the first region is a superior endplate and the second region is an inferior endplate;
providing an inflatable device configured for expansion with a working fluid;
inserting the inflatable device into the cavity that is the central portion of the vertebra; and
expanding the inflatable device to expand the cavity.

2. The method of claim 1, wherein the cavity is proximate a first region of the vertebral body endplate and separated from the first region by a layer of cancellous bone.

3. The method of claim 1, wherein the cavity has a boundary, a portion of which is cortical bone.

4. The method of claim 1, wherein the cavity has a boundary, a portion of which is cancellous bone.

5. The method of claim 1, wherein forming the cavity comprises a method of separating bone, the method of separating bone selected from the group consisting of shearing, cutting, scraping, and combinations thereof.

6. The method of claim 1, wherein the inflatable device is a balloon.

7. The method of claim 1, wherein the inflatable device is substantially non-compliant.

8. The method of claim 1, wherein the inflatable device is semi-compliant.

9. The method of claim 1, wherein expanding the inflatable device manipulates cortical bone to reduce a fracture.

10. The method of claim 1, further comprising filling the cavity with a material, wherein the material is a filling material selected from the group consisting of implant material, in-situ curable material, in-situ hardenable material, permanent material, resorbable material, penetrating material, and combinations thereof.

11. The method of claim 1, wherein the cavity is substantially axisymmetric.

12. The method of claim 1, wherein the cavity is substantially non-axisymmetric.

13. The method of claim 1, wherein a working end of the tissue cavitation device is transformable between a first shape for entry into the passage and a second shape for forming the cavity.

14. The method of claim 1, wherein the tissue cavitation device comprises:
   a shaft having a diameter and a longitudinal axis; and
   a flexible cutting element associated with the shaft, wherein the flexible cutting element is configured to assume a first shape for insertion and configured to assume a second shape suitable for forming the cavity that has a diameter greater than a diameter of the shaft when the shaft is rotated about the longitudinal axis of the shaft.

15. The method of claim 1, wherein the cavity is formed with rotational actuation of the tissue cavitation device.

16. The method of claim 1, wherein forming the passage in the vertebra precedes forming the cavity.

17. The method of claim 1, wherein forming the passage in the vertebra occurs substantially concomitantly with forming the cavity.

18. The method of claim 1, wherein expanding the inflatable device provides a distraction force.

* * * * *